United States Patent [19]

Siemensmeyer et al.

[11] Patent Number: 5,543,076

[45] Date of Patent: Aug. 6, 1996

[54] USE OF THE CHIRAL GROUP (1S, 4R)-1,4-DIHYDROXY-2-CYCLOPENTENYL IN THE PREPARATION OF POLAR, LIQUID-CRYSTALLINE COMPOUNDS

[75] Inventors: Karl Siemensmeyer, Frankenthal; Carsten Tschierske, Halle/Saale; Fritz Theil, Berlin; Detley Joachimi, Halle/Saale, all of Germany

[73] Assignee: BASF Aktiengesellschaft, Ludwigshafen, Germany

[21] Appl. No.: 307,105

[22] Filed: Sep. 16, 1994

Related U.S. Application Data

[63] Continuation of Ser. No. 41,407, Mar. 31, 1993, abandoned.

[30] Foreign Application Priority Data

Apr. 8, 1992 [DE] Germany ............... 42 11 692.9

[51] Int. Cl.⁶ ............ C09K 19/34; C09K 19/32; C09K 19/12; C07C 69/74

[52] U.S. Cl. ............. 252/299.61; 560/121; 252/299.62; 252/299.65; 252/299.66; 548/136

[58] Field of Search ............ 252/299.61, 299.62, 252/299.65, 299.66; 548/136; 560/121

[56] References Cited

U.S. PATENT DOCUMENTS

| | | | |
|---|---|---|---|
| 4,873,019 | 10/1989 | Krause et al. ............... | 252/299.61 |
| 5,269,965 | 12/1993 | Matsumura et al. ........... | 252/299.63 |
| 5,370,821 | 12/1994 | Matsumura et al. ........... | 252/299.63 |

*Primary Examiner*—C. H. Kelly
*Attorney, Agent, or Firm*—Keil & Weinkauf

[57] ABSTRACT

The chiral group of the formula

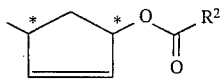

is used as a constituent of liquid-crystalline compounds.

3 Claims, No Drawings

USE OF THE CHIRAL GROUP (1S, 4R)-1,4-DIHYDROXY-2-CYCLOPENTENYL IN THE PREPARATION OF POLAR, LIQUID-CRYSTALLINE COMPOUNDS

This application is a continuation of application Ser. No. 08/041,407, filed on Mar. 31, 1993 abandoned.

The present invention relates to the use of (1S,4R)-1,4-dihydroxy-2-cyclopentenyl in the preparation of polar, liquid-crystalline compounds having the structure:

P—A—B—C  I where

P is a polymerizable unit or H, OH or ethenyl,

A is a flexible spacer,

B is a moiety built up from at least two aromatic rings linked to one another in a linear or approximately linear manner, and C is an optically active, polar, chiral moiety having the structure

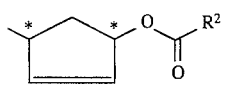  II where $R^2$ is linear or branched, chiral or achiral alkyl which may also be substituted by Cl, Br, F, CN or OH.

The present invention furthermore relates to the preparation of polymers from the monomers of the formula I if P is the group

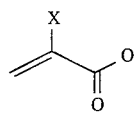  III where X is methyl, chlorine, bromine, CN or H, and to the use thereof for the production of recording layers for laser-optical and electrical recording elements and in electrophotography, for the production of latent charge images and for the production or as a constituent of liquid-crystalline display elements.

Chiral, smectic, liquid-crystalline materials which solidify in a glass-like manner with formation of a layer structure when cooled from the liquid-crystalline phase are, as is known, employed for many purposes in electro-optics, for example in optical storage systems (DE-A-38 27 603 and DE-A-39 17 196), electrophotography (DE-A-39 30 667), liquid-crystalline display elements, such as displays (Mol. Cryst. Liq. Cryst. 114, (1990) 151–187) and in electrical storage systems the materials simultaneously have ferroelectric properties (Ferroelectrics, 104 (1990) 241–256).

In the layer structure of ferroelectric $S_c^*$ phases, the molecular long axes within the individual layers are tilted with respect to the layer perpendicular z. The direction of this tilt is indicated by the director n, and the angle between z and n is known as the tilt angle θ. $S_c^*$ phases have two stable states with different directions of n; a rapid switching between these states can be effected by applying an electric field (electro-optical effect).

$S_c^*$ phases occur in both low-molecular-weight and polymeric liquid-crystalline materials; the essential properties of the $S_c^*$ phase correspond in both types of material.

However, the liquid-crystalline materials prepared hitherto have disadvantages, for example low spontaneous polarization, low phase widths, lack of a stable, tilted smectic phase at room temperature, or long response times.

Whether or not liquid-crystalline $S_c^*$ phases occur is determined to a considerable extent by all the constituent groups of the compounds, i.e. the spacer (A), the mesogenic groups (M) and the chiral groups (C); this means that extremely small changes in the molecular structure can induce $S_c^*$ phases or cause them to disappear.

Due to its structure and particular function, the chiral group in particular is of crucial importance for the occurrence of spontaneous polarization.

It is an object of the present invention to find chiral components for liquid-crystalline materials which do not affect the liquid-crystalline properties and at the same time induce high spontaneous polarization.

We have found that this object is achieved by using (1S,4R)-1,4-dihydroxy-2-cyclopentenyl as chiral group.

The parent liquid-crystalline precursors having the structure

P—A—B—  IV where P, A and B are as defined above, are disclosed in the literature, for example in DE-A-39 17 196.

The moiety P in low-molecular-weight ferroelectric materials is preferably hydrogen. For binding to polysiloxane or polyacrylic acid chains in a polymer-analogous reaction, P is preferably hydroxyl or ethenyl. By contrast, an acrylic acid substituted in the α-position by H, Cl, Br, CN or methyl is preferred for the preparation of materials which polymerize by means of free radicals or anionically.

The moiety A is preferably an alkylene group —(CH$_2$)$_n$— where n=2 to 20, preferably 6 to 11, it being possible for each third —CH$_2$— group to be replaced by —O— —S— (sulfur) or —NH—.

The mesogenic moiety B is built up from at least two aromatic rings linked to one another in a linear or approximately linear manner.

Examples of preferred groups B are those of the formulae V to IX:

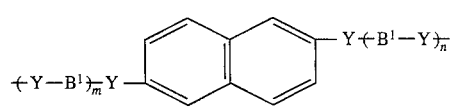  V

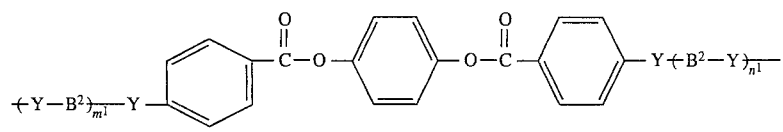  VI

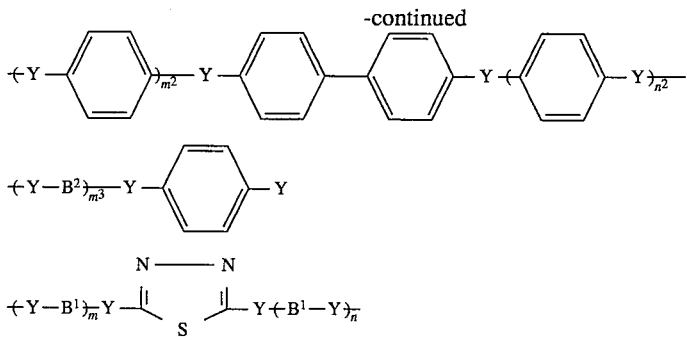

where

B¹ are identical or different p-phenylene or biphen-4,4'-ylene;

B² are identical or different p-phenylene, biphen-4,4'-ylene, naphth-2,6-ylene, 1,3,4-thiadiazolene or pyrimidylene, Y are identical or different and are preferably —O—, —COO—, —OCO— or a chemical bond, or alternatively —CH$_2$—O—, —O—CH$_2$—, —COS— or —SCO—, m and n are 0, 1 or 2, but m and n cannot simultaneously be 0, m¹ and n¹, independently of one another, are 0, 1 or 2, m² and n², independently of one another, are 0 or 1 and m³ is 1 or 2.

Examples of particularly preferred groups V are

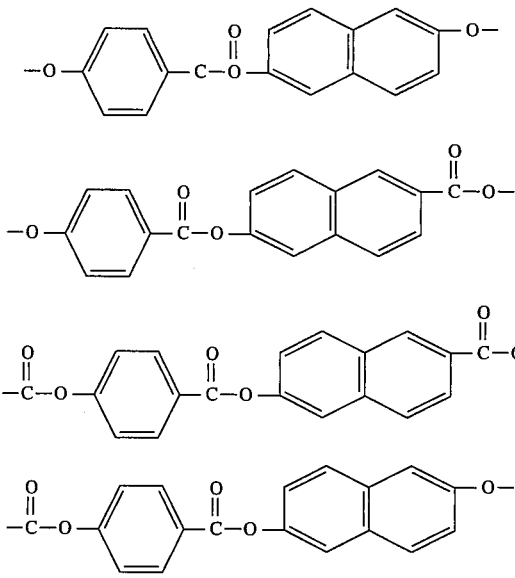

Examples of particularly preferred groups VI are

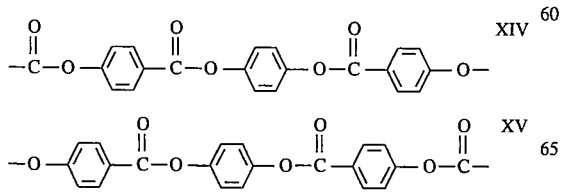

Examples of particularly preferred groups VII are

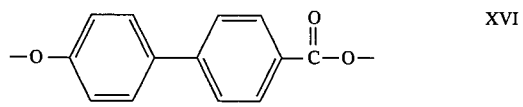

XVI

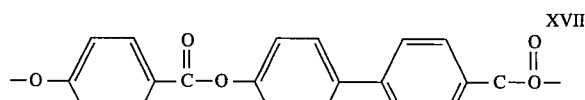

XVII

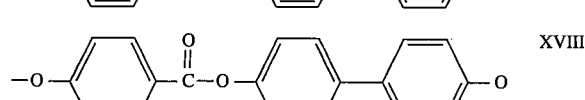

XVIII

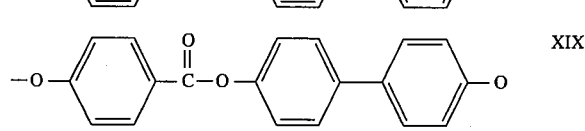

XIX

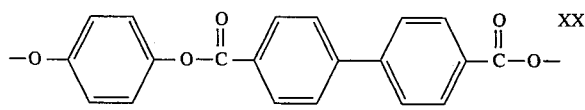

XX

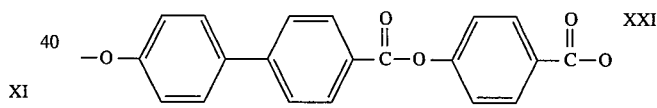

XXI

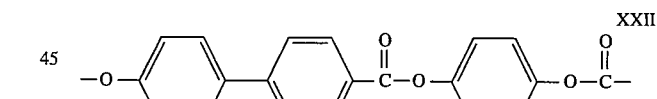

XXII

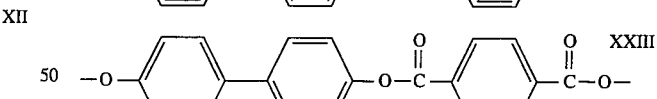

XXIII

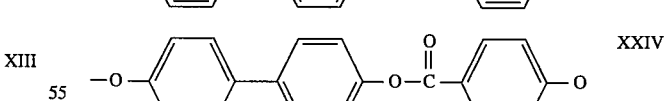

XXIV

Examples of particularly preferred groups VIII are

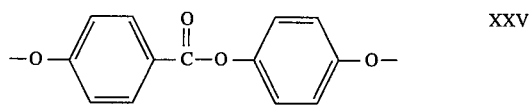

XXV

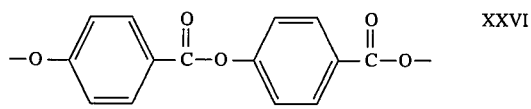

XXVI

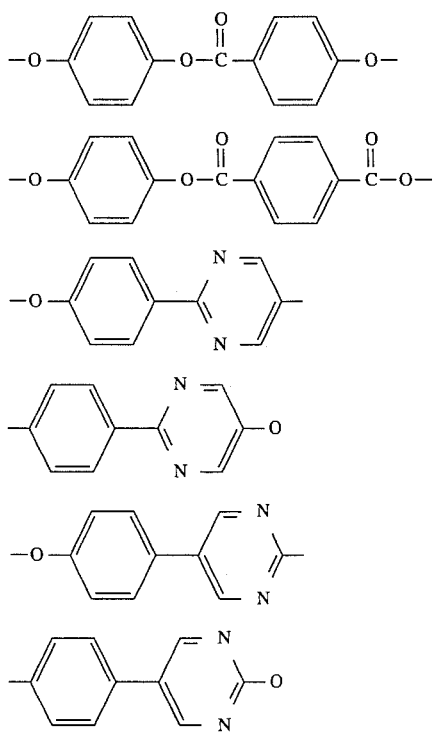

Examples of particularly preferred groups IX are

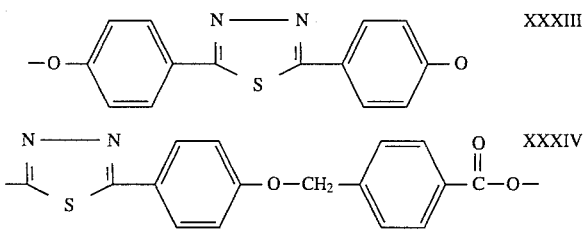

The chiral moiety C preferably has the following structure:

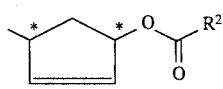

where $R^2$ is linear or branched, chiral or achiral alkyl, which may be substituted by Cl, Br, F, CN, methyl or OH and whose longest carbon chain has from 1 to 12 carbon atoms, but in which each third carbon atom may be replaced by O, NH or S.

Examples of C are:

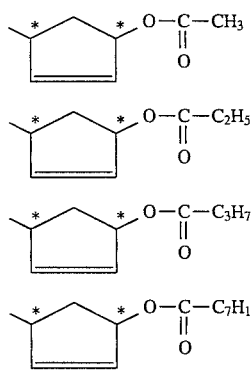

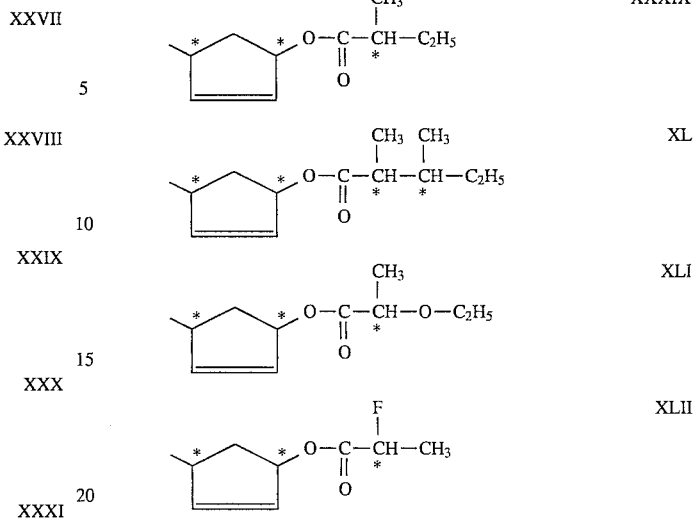

The novel units P—A—B in which P, A and B are as defined above are in principle accessible by syntheses which are known in general terms, as described in DE-A-39 17 196, Mol. Cryst. Liq. Cryst. 191 (1991) 223 and Mol. Cryst. Liq. Cryst. 191 (1991) 231.

The preparation of optically active (1S,4R)-1,4-dihydroxy-2-cyclopentene was described for the first time in Angew. Chem. 68 (1956), 248.

The phase transition temperatures were determined using a Boetius heating stage microscope and are uncorrected.

The spontaneous polarization was determined by the bridge method of Diamant et al. (Rev. Sci. Instr. 28 (1957) 30).

General procedure for the preparation of
(1S,4R)-2-(4-octyloxyphenyl)-
5-[4-carboxyl-2-cyclopentenyloxy)phenyl]-
1,3,4-thiadiazole by Mitsunobu etherification.

3.0 mmol of the substituted phenol, 4.5 mmol of triphenylphosphine (1.2 g) and 4.5 mmol of the cyclopentenol in 25 ml of absolute THF are introduced into a 50 ml flask fitted with CaCl₂ tube and septum stopper. 4.5 mmol (0.75 ml) of diethyl azodicarboxylate are added dropwise over the course of 10 minutes at from 0° to 5° C. with stirring. The mixture is then stirred at room temperature for 24 hours, and the majority of the solvent is then removed by distillation. Triphenylphosphine oxide is removed by recrystallization twice from methanol/water (10/1). Subsequent repeated recrystallization from ethanol gives the pure target compound.

EXAMPLES

EXAMPLE 1

Preparation of
(1S,4R)-2-(4-octyloxyphenyl)-5-[4-(1-acetoxy-2-cyclopentenyloxy)phenyl]-1,3,4-thiadiazole

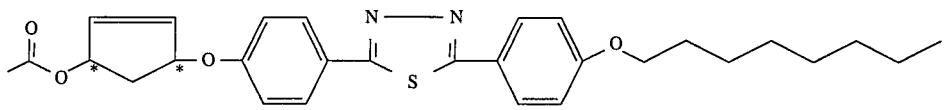

The general preparation procedure was followed using
3 mmol of 4-octyloxyphenyl-5-(4-hydroxyphenyl)-1,3,4-thiadiazole (1.15 g)
4.5 mmol of (1S, 4R)-4-hydroxy-2-cyclopentenyl acetate (0.64 g)
4.5 mmol of triphenylphosphine (1.2 g)
4.5 mmol of diethyl azodicarboxylate (0.75 ml)
Yield: 0.81 g of (1S,4R)-2-(4-octyloxyphenyl)-5-[4-(1-acetoxy- 2-cyclopentenyloxy)phenyl]-1,3,4-thiadiazole (53%)
Phase behavior: C 89.5 $S_c^*$ 159 N* 181.5 I
The spontaneous polarization at 129° C. is 86 nC cm$^{-2}$

EXAMPLE 3

Preparation of (1S,4R)-2-(4-octyloxyphenyl)-5-[4-(1-butoxy-2-cyclopentenyloxy)phenyl]-1,3,4-thiadiazole Amounts employed:
3 mmol of 4-octyloxyphenyl-5-(4-hydroxyphenyl)-1,3,4-thiadiazole (1.15 g)
4.5 mmol of (1S,4R)-4-hydroxy-2-cyclopentenyl acetate (0.64 g)
4.5 mmol of triphenylphosphine (1.2 g)
4.5 mmol of diethyl azodicarboxylate (0.75 ml)

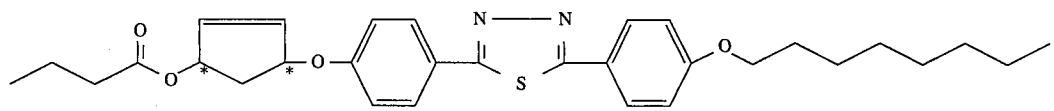

EXAMPLE 2

Preparation of (1S,4R)-2-(4-octyloxyphenyl)-5-[4-(1-propoxy-2-cyclopentenyloxy)phenyl]-1,3,4-thiadiazole Amounts employed:
3 mmol of 4-octyloxyphenyl-5-(4-hydroxyphenyl)-1,3,4-thiadiazole (1.15 g)
4.5 mmol of (1S,4R)-4-hydroxy-2-cyclopentenyl acetate (0.64 g)
4.5 mmol of triphenylphosphine (1.2 g)
4.5 mmol of diethyl azodicarboxylate (0.75 ml)

Yield: 0.9 g (60%)
Phase behavior: C 99 $S_c$ 167 N* 172 I
The spontaneous polarization at 137° C. is 78 nC cm$^{-2}$.

EXAMPLE 4

Preparation of (1S,4R)-2-(4-octyloxyphenyl)-5-[4-(1-octoxy-2-cyclopentenyloxy)phenyl]-1,3,4-thiadiazole Amounts employed:
3 mmol of 4-octyloxyphenyl-5-(4-hydroxyphenyl)-1,3,4-thiadiazole (1.15 g)
4.5 mmol of (1S,4R)-4-hydroxy-2-cyclopentenyl . . .

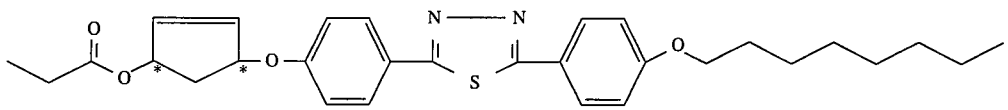

Yield: 0.83 g (55%)
Phase behavior: C 92 $S_c$ 167 $S_A$ 177 I
The spontaneous polarization at 137° C. is 85 nC cm$^{-2}$.

4.5 mmol of triphenylphosphine (1.2 g)
4.5 mmol of diethyl azodicarboxylate (0.75 ml)

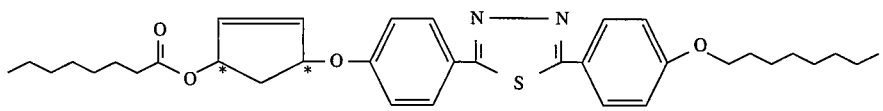

Yield: 0.9 g (50%)
Phase behavior: C 80.5 $S_x$ 91 $S_c^*$ 164.5 N* 167 I
The spontaneous polarization at 144° C. is 62 nC cm$^{-2}$.
Preparation of(1S,4R)-2-undecyl-5-[4-(1-acetoxy- 2-cyclopentenyloxycarboxybenzyloxy)phenyl]-1,3,4-thiadiazole
Amounts employed:

3.1 mmol of (1S,4R)-4-hydroxy-2-cyclopentenol acetate (cyclopentenol)

3.1 mmol of dicyclohexylcarbodiimide (DCC)

0.1 mmol of pyrrolidinopyridine (PP)

3.1 mmol of 2-undecyl-5-[4-carboxybenzylphenyl ether]-1,3,4-thiadiazole (carboxylic acid)

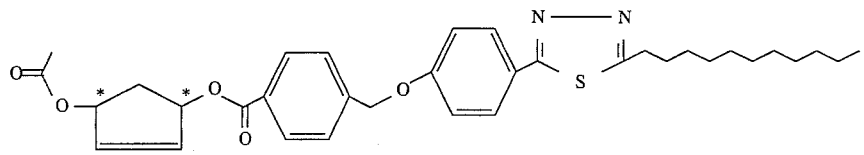

3.1 mmol of the cyclopentenol, 3.1 mmol of DCC and 0.1 mmol of PP are dissolved in $CH_2Cl_2$ in a 100 ml flask fitted with a $CaCl_2$ tube, 3.1 mmol of the carboxylic acid are added at 0°–5° C. with ice cooling, and the mixture is stirred at room temperature for 24 hours. The precipitated urea is filtered off, the solvent is removed by evaporation, and the crude product is recrystallized a number of times from ethanol.

Yield: 0.83 g (=60%)

Phase behavior: C 103.5 ($S_c^*$ 80) $S_A$ 145 I

The spontaneous polarization at 78° C. is 8 nC $cm^{-2}$.

We claim:

1. A liquid-crystalline compound having the structure:

$$P\text{—}A\text{—}B\text{—}C \qquad I$$

where

P is OH or

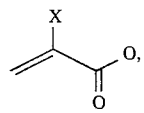

where X is methyl, Cl, Br, CN or H,

A is an alkylene group $-(CH_2)_n-$ where n=2 to 20, wherein each third $-CH_2-$ group is optionally replaced by —O— (oxygen), —S— (sulfur) or —NH—;

B is a moiety made up of at least two aromatic rings linked to one another in a linear or substantially linear manner selected from the group consisting of

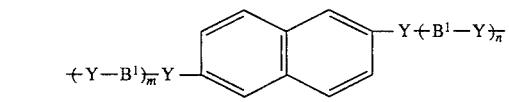
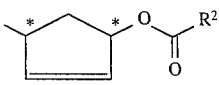
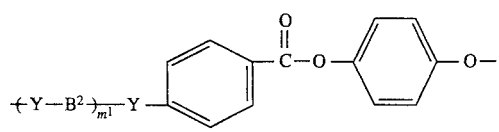

where $B^1$ are identical or different p-phenylene or biphen-4,4'-ylene;

$B^2$ are identical or different p-phenylene, biphen-4,4'-ylene, naphth-2,6-ylene, 1,3,4-thiadiazolene or pyrimidylene, Y are identical or different and are —O—, —COO—, —OCO— or a chemical bond, or alternatively $-CH_2-O-$, —O—, $-O-CH_2$, —COS— or —SCO—, m and n are 0, 1 or 2, but m and n cannot simultaneously be 0, $m^1$ and $n^1$, independently of one another, are 0, 1 or 2, $m^2$ and $n^2$, independently of one another are 0 or 1 and $m^3$ is 1 or 2, C is an optically active, polar, chiral moiety having the structure where $R^2$ is a linear or branched $C_1$–$C_{12}$-alkyl radical which is unsubstituted or substituted by F, Cl, Br, CN, or OH.

2. The compound of claim 1, wherein P is OH.

3. A liquid crystalline medium comprising the liquid crystalline compound of claim 1.

* * * * *

UNITED STATES PATENT AND TRADEMARK OFFICE
CERTIFICATE OF CORRECTION

PATENT NO.: 5,543,076

DATED: August 6, 1996

INVENTOR(S): SIEMENSMEYER et al.

It is certified that error appears in the above-identified patent and that said Letters Patent is hereby corrected as shown below:

On the title page, item [75], the third named inventor's name "Detley" should read --Detlev--.

Column 10, claim 1, line 39, delete "—O—".

Signed and Sealed this

Fourteenth Day of January, 1997

Attest:

BRUCE LEHMAN

*Attesting Officer*  *Commissioner of Patents and Trademarks*